United States Patent [19]
Fiddes et al.

[11] Patent Number: 5,439,818
[45] Date of Patent: Aug. 8, 1995

[54] DNA ENCODING HUMAN RECOMBINANT BASIC FIBROBLAST GROWTH FACTOR

[75] Inventors: John C. Fiddes, Palo Alto; Judith A. Abraham, Sunnyvale, both of Calif.

[73] Assignee: Scios Nova Inc., Mountain View, Calif.

[21] Appl. No.: 809,163

[22] Filed: Dec. 16, 1985

Related U.S. Application Data

[63] Continuation-in-part of Ser. No. 775,521, Sep. 12, 1985, abandoned.

[51] Int. Cl.6 .................. C12N 5/10; C12N 1/21; C12N 15/16; C12N 15/85
[52] U.S. Cl. ............... 435/240.2; 435/252.33; 435/320.1; 536/23.5; 536/23.51
[58] Field of Search .............. 435/68, 91, 170, 172.1, 435/172.3, 240.1, 253, 320, 849, 69.1, 69.6, 91.1, 252.33, 320.1; 536/27, 23.51, 23.5; 935/6, 8, 9, 22, 23, 24, 29, 32, 33, 34, 36, 38, 39, 59, 60, 61, 70, 72, 73

[56] References Cited

U.S. PATENT DOCUMENTS

| | | | |
|---|---|---|---|
| 4,296,100 | 10/1981 | Franco | 424/565 |
| 4,378,347 | 3/1983 | Franco | 424/565 |
| 4,399,216 | 8/1983 | Axel et al. | 435/6 |
| 4,444,760 | 4/1984 | Thomas, Jr. | 514/21 |

OTHER PUBLICATIONS

Ammerer (1983) in "Methods in Enzymology, vol. 101" ed. Wu et al. Academic Press, N.Y., N.Y. pp. 192–200.
Suggs et al, 1981. *PNAS* 78:6613–6617.
Dalbadie-McFarland et al. 1982 *PNAS* 79:6409–6413.
Maniatis et al. 1982 Molecular Cloning: A Laboratory Manual. Cold Spring Harbor Laboratory pp. 211–246, 269–308 and 403–434.
Southern et al. 1982 In Eukaryotic Viral Vectors Gluzman (ed) Cold Spring Harbor Laboratory pp. 41–45.
Bohlen, P. et al, *The EMBO Jour*, (1985) 4:1951–1956.
Bohlen, P. et al, *Proc. Natl Acad. Sci* USA (1984) 81:5364.
Davidson, J. M., et al *J Cell Biol*, (1985) 100:1219.
Folkman, J. et al, *Science* (1983) 221:719–725.
Gospodarowicz, D. et al., *Biochem & Biophy Res Comm*, (1985) 2:554–562.
Gospondarowicz, D. et al, *Proc. Natl. Acad. Sci* USA 81:6963–6967.
Hunt, T. K. *Jour of Trauma*, (1984) 24:S39–S49.
Lobb, R. R., et al *Biochemistry* (1984) 23:6296–6299.
Maciag, T. et al *Science* (1984) 225:932–935.
Shing, Y. et al, *Science* (1984) 223:1296–1299.
Klagsbrun, M. et al *Proc. Natl. Acad. Sci.* USA (1985) 82:805–809.
Sporn, M. et al *Science* (1983) 219:1329–1330.
Thomas, K. A., et al *Proc. Natl. Acad. Sci.* USA (1984) 81:357–361.
Sullivan, R. et al *Endothelial Growth Factors Abstracts* 108a:409.
Jackson, J. P. et al *The Lancet* (1985) 244–246.
Sullivan, R. et al *J of Biol Chem* (1985) 260:2399–2403.

*Primary Examiner*—Richard A. Schwartz
*Assistant Examiner*—Douglas Gurian-Sherman
*Attorney, Agent, or Firm*—Burns, Doane, Swecker & Mathis

[57] ABSTRACT

Disclosed herein are the DNA sequences encoding human and bovine acidic and basic fibroblast growth factors (FGF). Expression of these sequences results in practical amounts of proteins useful in effecting wound healing.

17 Claims, 12 Drawing Sheets

```
  1                              27                                              54
AAT TCA TGC CTC TTT CTC TCC TTT TGT TGG TAG ACG ACT TCA GCC TCT GTC CTT 81                                             108
TAA TTT TAA AGT TTA TGC CCC ACT TGT ACC CCT CGT CTT TTG GTG ATT TAG AGA 135                                             162
TTT TCA AAG CCT GCT CTG ACA CAG ACT CTT CCT TGG ATT GCA ACT TCT CTA CTT 189                                             216
TGG GGT GGA AAC GGC TTC TCC GTT TTG AAA CGC TAG CGG GGA AAA AAT GGG GGA 243                                             270
GAA AGT TGA GTT TAA ACT TTT AAA AGT TGA GTC ACG GCT GGT TGC GCA CGA AAA 297                                             324
GCC CCG CAG TGT GGA GAA AGC CTA AAC GTG GTT TGG GTG GTG CGG GGG TTG GGC 351                                             378
GGG GGT GAC TTT TGG GGG ATA AGG GGC GGT GGA GCC CAG GGA ATG CCA AAG CCC 405                                             432
TGC CGC GGC CTC CGA CGC GCG CCC CCC GCC CCT CGC CTC TCC CCC GCC CCC GAC 459                                             486
TGA GGC CGG GCT CCC CGC CGG ACT GAT GTC GCG CGC TTG CGT GTT GTG GCC GAA 513                                             540
GCC GCC GAA CTC AGA GGC CGG CCC CAG AAA ACC CGA GCG AGT AGG GGG CGG CGC 567                                             594
GCA GGA GGG AGG AGA ACT GGG GGC GCG GGA GGC TGG TGG GTG TGG GGG GTG GAG 621                                             648
ATG TAG AAG ATG TGA CGC CGC GGC CCG GCG GGT GCC AGA TTA GCG GAC GGC TGC 675                                             702
CCG CGG TTG CAA CGG GAT CCC GGG CGC TGC AGC TTG GGA GGC GGC TCT CCC CAG 729                                             756
GCG GCG TCC GCG GAG ACA CCC ATC TGT GAA CCC CAG GTC CCG GGC CGC CGG CTC 783                                             810
GCC GCG CAC CAG GGG CCG GCG GAC AGA AGA GCG GCC GAG CGG CTC GAG GCT GGG 837                                             864
GGA CCG CGG GCG CGG CCG CGC GCT GCC GGG CGG GAG GCT GGG GGG CCG GGG CCG 891                                             918
GGG CCG TGC CCG GAG CGG GTC GGA GGC CGG GGC CGG GGC CGG GGG ACG GCG GCT 945                                             972
CCC CGC GCG GCT CCA GCG GCT CGG GGA TCC CGG CCG GCC CCC GCA GGG ACC ATG
                                                                         MET
                                                                          1
```

FIG. IA

```
                                        999                                              1026
GCA GCC GGG AGC ATC ACC ACG CTG CCC GCC TTG CCC GAG GAT GGC GGC AGC GGC
Ala Ala Gly Ser Ile Thr Thr Leu Pro Ala Leu Pro Glu Asp Gly Gly Ser Gly 1053                                              1080
GCC TTC CCG CCC GGC CAC TTC AAG GAC CCC AAG CGG CTG TAC TGC AAA AAC GGG
Ala Phe Pro Pro Gly His Phe Lys Asp Pro Lys Arg Leu Tyr Cys Lys Asn Gly
 20                                          30

1107                                        1134
GGC TTC TTC CTG CGC ATC CAC CCC GAC GGC CGA GTT GAC GGG GTC CGG GAG AAG
Gly Phe Phe Leu Arg Ile His Pro Asp Gly Arg Val Asp Gly Val Arg Glu Lys
        40                                           50

1161                                              1188
AGC GAC CCT CAC ATC AAG CTA CAA CTT CAA GCA GAA GAG AGA GGA GTT GTG TCT
Ser Asp Pro His Ile Lys Leu Gln Leu Gln Ala Glu Glu Arg Gly Val Val Ser
                  60                                       70

1215                                              1242
ATC AAA GGA GTG TGT GCT AAC CGT TAC CTG GCT ATG AAG GAA GAT GGA AGA TTA
Ile Lys Gly Val Cys Ala Asn Arg Tyr Leu Ala MET Lys Glu Asp Gly Arg Leu
                       80                                              90

1269                                              1296
CTG GCT TCT AAA TGT GTT ACG GAT GAG TGT TTC TTT TTT GAA CGA TTG GAA TCT
Leu Ala Ser Lys Cys Val Thr Asp Glu Cys Phe Phe Phe Glu Arg Leu Glu Ser
                              100

1323                                              1350
AAT AAC TAC AAT ACT TAC CGG TCA AGG AAA TAC ACC AGT TGG TAT GTG GCA TTG
Asn Asn Tyr Asn Thr Tyr Arg Ser Arg Lys Tyr Thr Ser Trp Tyr Val Ala Leu
110                                     120

1377                                              1404
AAA CGA ACT GGG CAG TAT AAA CTT GGA TCC AAA ACA GGA CCT GGG CAG AAA GCT
Lys Arg Thr Gly Gln Tyr Lys Leu Gly Ser Lys Thr Gly Pro Gly Gln Lys Ala
         130                                          140

1431                                              1458
ATA CTT TTT CTT CCA ATG TCT GCT AAG AGC TGA TTT TAA TGG CCA CAT CTA ATC
Ile Leu Phe Leu Pro MET Ser Ala Lys Ser
                150              155
```

FIG. 1B

```
                              1485                                              1512
TCA TTT CAC ATG AAA GAA GAA GTA TAT TTT AGA AAT TTG TTA ATG AGA GTA AAA
                              1539                                              1566
GAA AAT AAA TGT GTA TAG CTC AGT TTG GAT AAT TGG TCA AAC AAT TTT TTA TCC
                              1593                                              1620
AGT AGT AAA ATA TGT AAC CAT GCC CAG TAA AGA AAA ATA ACA AAA GTT GTA AAA
                              1647                                              1674
TGT ATA TTC TCC CTT TTA TAT TGC ATC TGC TGT TAC CCA GTG AAG CTT ACC TAG
                              1701                                              1728
AGC AAT GAT CTT TTT CAC GCA TTT GCT TTA TTC GAA AAG AGG CTT TTA AAA TGT
                              1755                                              1782
GCA TGT TTA GAA AAC AAA ATT TCT TCA TGG AAA TCA TAT ACA TTA GAA AAT CAC
                              1809                                              1836
AGT CAG ATG TTT AAT CAA TCC AAA AAT GTC CAC TAT TTC TTA TGT CAT TCG TTA
                              1863                                              1890
GTC TAC ATG TTT CTA AAC ATA TAA ATG TGA ATT TAA TCA ATT CCT TTC ATA GTT
                              1917                                              1944
TTA TAA TTC TCT GGC AGT TCC TTA TGA TAG AGT TTA TAA AAC AGT CCT GTG TAA
                              1971
ACT GCT GGA AGT TCT TCC GGA ATT C
```

FIG. IC

```
                                           27                                          54
TGC ATT TTG TGC CTT TGC TGG AAG AAC CGA CTA CAG GTT TGT TCA ATT TCT TAC

81                            ·            108
AGT CTT GAA AGC GCC ACA AGC AGC AGC TGC TGA GCC ATG GCT GAA GGG GAA ATC
                                                    MET Ala Glu Gly Glu Ile
                                                     1

135                                         162
ACC ACC TTC ACA GCC CTG ACC GAG AAG TTT AAT CTG CCT CCA GGG AAT TAC AAG
Thr Thr Phe Thr Ala Leu Thr Glu Lys Phe Asn Leu Pro Pro Gly Asn Tyr Lys
             10                                       20

189                                         216
AAG CCC AAA CTC CTC TAC TGT AGC AAC GGG GGC CAC TTC CTG AGG ATC CTT CCG
Lys Pro Lys Leu Leu Tyr Cys Ser Asn Gly Gly His Phe Leu Arg Ile Leu Pro
                      30                                          40

243                                         270
GAT GGC ACA GTG GAT GGG ACA AGG GAC AGG AGC GAC CAG CAC ATT CAG CTG CAG
Asp Gly Thr Val Asp Gly Thr Arg Asp Arg Ser Asp Gln His Ile Gln Leu Gln
                              50                                                       60

297                                         324
CTC AGT GCG GAA AGC GTG GGG GAG GTG TAT ATA AAG AGT ACC GAG ACT GGC CAG
Leu Ser Ala Glu Ser Val Gly Glu Val Tyr Ile Lys Ser Thr Glu Thr Gly Gln
                                      70

351                                         378
TAC TTG GCC ATG GAC ACC GAC GGG CTT TTA TAC GGC TCA CAG ACA CCA AAT GAG
Tyr Leu Ala MET Asp Thr Asp Gly Leu Leu Tyr Gly Ser Gln Thr Pro Asn Glu
         80                                          90

405                                         432
GAA TGT TTG TTC CTG GAA AGG CTG GAG GAG AAC CAT TAC AAC ACC TAT ATA TCC
Glu Cys Leu Phe Leu Glu Arg Leu Glu Glu Asn His Tyr Asn Thr Tyr Ile Ser
             100                                         110

459                                         486
AAG AAG CAT GCA GAG AAG AAT TGG TTT GTT GGC CTC AAG AAG AAT GGG AGC TGC
Lys Lys His Ala Glu Lys Asn Trp Phe Val Gly Leu Lys Lys Asn Gly Ser Cys
                     120                                          130

513                                         540
AAA CGC GGT CCT CGG ACT CAC TAT GGC CAG AAA GCA ATC TTG TTT CTC CCC CTG
Lys Arg Gly Pro Arg Thr His Tyr Gly Gln Lys Ala Ile Leu Phe Leu Pro Leu
                             140                                                      150

567                                         594
CCA GTC TCT TCT GAT TAA AGA GAT CTG TTC TGG GTG TTG ACC ACT CCA GAG AAG
Pro Val Ser Ser Asp
                 155

621
TTT CGA GGG GTC CTC ACC TGG TTG ACC CAA AAA TGT TCC CTT GA
```

FIG. 2

(basic/acidic)

```
                                    HEPARIN                RECEPTOR
                                    BINDING DOMAIN         BINDING DOMAIN
    1          10           20           30           40           50           60
    MAAGSITTTLPALPEDGGSGAFPPGHFKDPKRLYCKNGGFFLRIHPDGRVDGVREKSDPHI
    ::  :: ::         ::   ::    ::: ::: ::: :::  :: ::  :::  ::
    MAEGEITTFTALTEKFNL---PPGNYKKPKLLYCSNGGHFLRILPDGTVDGTRDRSDQHI
    1          10           20           30           40           50

70           80           90          100          110          120
    KLQLQAEERGVVSIKGVCANRYLAMKEDGRLLASKCVTDECFFFERLESNNYNTYRSRKY
    :::: ::  :::: :: ::::    :::::::::   ::  :: ::::::: :: :: :
    QLQLSAESVGEVYIKSTETGQYLAMDTDGLLYGSQTPNEECLFLERLEENHYNTYISKKH
    60           70           80           90          100          110

130          140          150
    TS--WYVALKRTGQYKLGSKTGPGQKAILFLPMSAKS
    ::    :: ::::: ::::   ::::::: :: ::
    AEKNWFVGLKKNGSCKRGPRTHYGQKAILFLPLPVSSD
    120          130          140          150
         ↑
    HEPARIN BINDING DOMAIN
```

FIG. 3

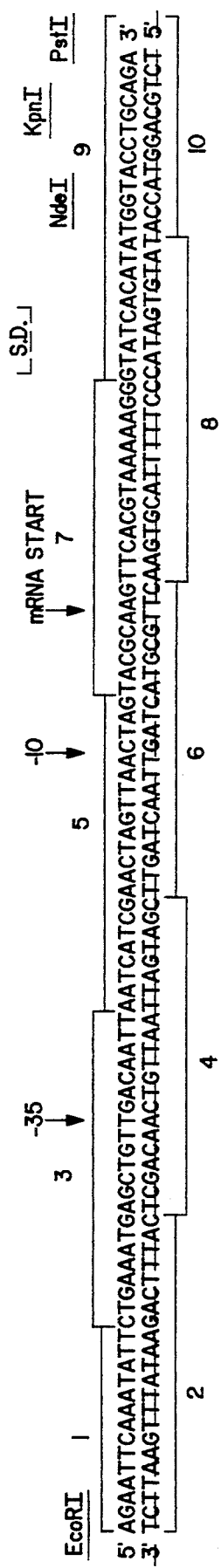
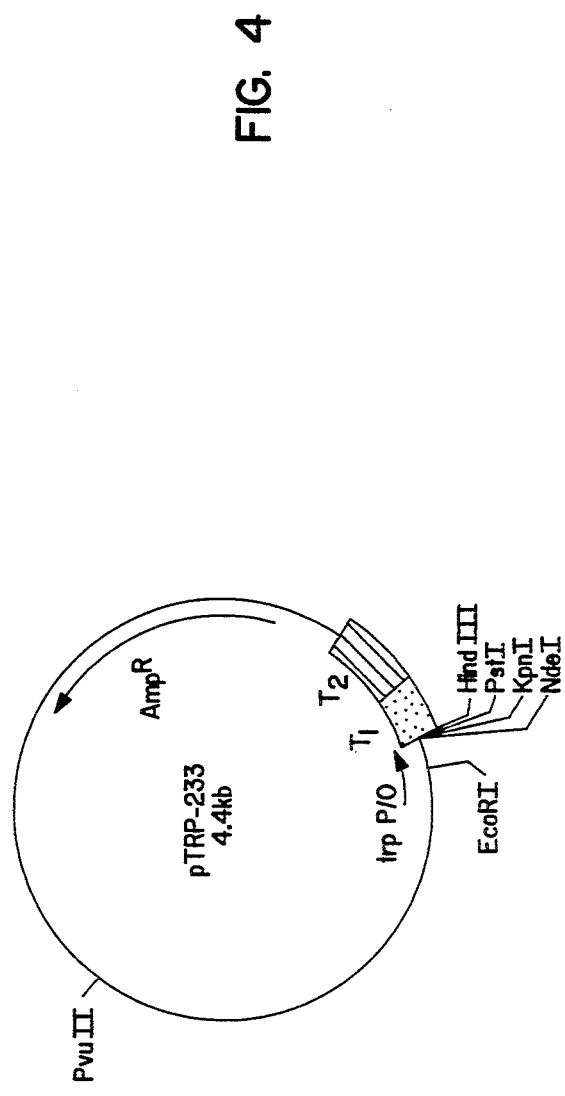
FIG. 4

AGCTGCTGAGCCATGGCTGAAGGAGAAACCACGACCTTCACGGCCCTGACTGAGAAG
AluI

| TTT | AAC | CTG | CCT | CTA | GGC | AAT | TAC | AAG | AAG | CCC | AAG | CTC | CTC | TAC | TGC | AGC | AAC |
|-----|-----|-----|-----|-----|-----|-----|-----|-----|-----|-----|-----|-----|-----|-----|-----|-----|-----|
| Phe | Asn | Leu | Pro | Leu | Gly | Asn | Tyr | Lys | Lys | Pro | Lys | Leu | Leu | Tyr | Cys | Ser | Asn |
| 1   |     |     |     |     |     |     |     |     | 10  |     |     |     |     |     |     |     |     |

| GGG | GGC | TAC | TTC | CTG | AGA | ATC | CTC | CCA | GAT | GGC | ACA | GTG | GAT | GGG | ACG | AAG | GAC |
|-----|-----|-----|-----|-----|-----|-----|-----|-----|-----|-----|-----|-----|-----|-----|-----|-----|-----|
| Gly | Gly | Tyr | Phe | Leu | Arg | Ile | Leu | Pro | Asp | Gly | Thr | Val | Asp | Gly | Thr | Lys | Asp |
|     | 20  |     |     |     |     |     |     |     |     |     |     |     |     | 30  |     |     |     |

| AGG | AGC | GAC | CAG | CAC | A GTAAGCACCCATCTCACATTTCTGGTATCTTCCTTACTCAGGGACAGGA |
|-----|-----|-----|-----|-----|-----|
| Arg | Ser | Asp | Gln | His |     |
|     |     |     |     | 40  |     |

GAAGGGAGAATAGGGAGAATAGCTAAGGGCT
                      AluI

FIG. 7

```
                                           9                                    27
acidic
FGF                       lys lys pro lys leu leu tyr cys ser asn gly gly tyr phe leu arg ile leu pro known
coding            5'  AAG AAG CCC AAG CTC CTC TAC TGC AGC AAC GGG GGC TAC TTC CTG AGA ATC CTC CCA   3'
sequence 18                                   36
basic
FGF                       lys asp pro lys arg leu tyr cys lys asn gly gly phe phe leu arg ile his pro potential
coding            5'  AAG GAC CCC AAG CGC CTC TAC TGC AAG AAC GGG GGC TTC TTC CTG AGA ATC CAC CCA   3'
sequence probe
1098              3'  TTC CTG GGG TTC GCG GAG ATG ACG TTC TTG CCC CCG AAG A             5' probe          3'  G ATG ACG TTC TTG CCC CCG AAG AAG GAC TCT TAG GTG GGT    5'
                  1097
```

FIG. 9

DNA ENCODING HUMAN RECOMBINANT BASIC FIBROBLAST GROWTH FACTOR

CROSS REFERENCE TO RELATED APPLICATION

This is a continuation-in-part of U.S. Ser. No. 775,521 filed 12 Sept. 1985, now abandoned.

TECHNICAL FIELD

The invention relates to recombinant production of growth factors important for constructing vascular systems in healing tissues. In particular, the genes encoding bovine and human basic and acidic fibroblast growth factors (FGF) are cloned and expressed.

BACKGROUND ART

The process of healing when tissue is subjected to trauma, such as wounding or burns, is an extremely complex one, but it is known to be mediated by a number of protein factors. These factors are essential to the growth and differentiation of the cells which serve to replace the tissue destroyed. A number of candidate factors have been identified on the basis of the ability of extracts from various tissues, such as brain, pituitary, and hypothalamus, to stimulate the mitosis of cultured cell lines. Numerous shorthand names have been applied to the active factors in these extracts, including platelet-derived growth factor (PDGF), macrophage-derived growth factor (MDGF), epidermal growth factor (EGF), tumor angiogenesis factor (TAF), endothelial cell growth factor (ECGF), fibroblast growth factor (FGF), hypothalamus-derived growth factor (HDGF), retina-derived growth factor (RDGF), and heparin-binding growth factor (HGF). (See, for example, Hunt, T. K., *J Trauma* (1984) 24:S39–S49; Lobb, R. R., et al, *Biochemistry* (1984) 23:6295–6299).

Folkman, J., et al, *Science* (1983) 221:719–725, reported that one of the processes involved in wound healing, the formation of blood vessels, is profoundly affected in tumors by heparin. From this and other studies, it is clear that heparin specifically binds to protein(s) associated with a number of these growth factor activities, and therefore heparin has been used as a purification tool. It has been shown that the affinity of growth factors for heparin is independent of overall ionic charge, since both positively and negatively charged factors are bound (Maciag, T., et al, *Science* (1984) 225:932–935; Shing, Y., et al, *Science* (1984) 223:1296–1299; Klagsbrun, M., et al, *Proc Natl Acad Sci* (USA) (1985) 82:805–809). The capacity to bind or not to bind to heparin is one measure of differentiation between the activities in the various extracts. For example, EGF and PDGF do not bind strongly to heparin; in fact, EGF does not bind to heparin at all. The other factors above do show strong heparin binding. However, it is believed that acidic brain FGF, ECGF, RDGF, and HGF-α are in fact the same factor. Similarly, it is also believed that pituitary FGF, cationic brain FGF, TAF and HGF-β are the same protein. (Lobb, R.R., et al (supra)).

Using heparin affinity chromatography, basic fibroblast growth factors exhibiting a potent mitogenic activity for capillary endothelium have been isolated from rat chondrosarcoma (Shing, Y., et al, supra) and from bovine cartilage (Sullivan, R., et al, *J Biol Chem* (1985) 260:2399–2403). Thomas, K. A, et al, *Proc Natl Acad Sci* (USA) (1984) 81:357–361, U.S. Pat. No. 4,444,760, purified two heterogeneous forms of an acidic bovine brain fibroblast growth factor having molecular weights of 16,600 and 16,800 daltons. Gospodarowicz and collaborators showed the presence in both bovine brains and pituitaries of basic fibroblast growth factor activities and purified these proteins using heparin-affinity chromatography in combination with other purification techniques (Bohlen, P., et al, *Proc Natl Acad Sci* (USA) (1984) 81:5364–5368; Gospodarowicz, D., et al (ibid) 6963–6967). These factors also have molecular weights of approximately 16 kd, as does a similar factor isolated from human placenta (Gospodarowicz, D., et al, *Biochem Biophys Res Comm* (1985) 128:554–562). The basic FGF native proteins have been alleged to be useful in treatment of myocardial infarction (U.S. Pat. Nos. 4,296,100 and 4,378,347).

An N-terminal sequence for acidic FGF derived from bovine brain tissue (Bohlen, P., et al, *EMBO J* (1985) 4:1951–1956) and the complete sequence for basic FGF derived from bovine pituitary have been determined (Esch, F., et al, *Proc Natl Acad Sci* (USA), 82, 6507–6511, 1985. Homogeneous preparations were obtained and showed potent mitogenic activity in vitro assays with endothelial cells (basic FGF has an $ED_{50}$ of 60 pg/ml; acidic FGF has an $ED_{50}$ of about 6,000 pg/ml).

Since these and other growth factors are clearly effective in promoting the healing of tissue subjected to trauma (see, e.g., Sporn, M. B., et al, *Science* (1983) 219:1329–1331; Davidson, J. M., et al, *J. C. B.* (1985) 100:1219–1227), it would be desirable to insure their availability in large quantities and in a form free from any toxic or infectious impurities. Of course, the human form of the protein is preferred, and perhaps required, for therapeutic use. Clearly practical availability cannot be achieved from natural human sources, as obtaining a pure preparation involves an approximately 35,000-fold purification. Even if human cadavers were otherwise a practical source, complete purification would be crucial due to the possibility of transmitting AIDS, hepatitis, or other disease. The recent experience with Creutzfeld-Jacob Syndrome (Powell-Jackson et al, *Lancet* (1985) ii:244–246) precludes the use of human pituitaries as a source. Therefore, recombinant techniques are particularly suitable to apply to the production of these proteins. The invention herein provides the means whereby acidic and basic FGF can be obtained in practical quantities and in pure, uncontaminated form.

DISCLOSURE OF THE INVENTION

The invention provides the tools for synthesis and manipulation of fibroblast growth factors useful in effecting accelerated healing of wounds, bone fractures, burn tissue, or other trauma. Cloning and expression of the genes encoding these factors are provided by the methods and materials of the invention.

In one aspect, the invention relates to recombinant DNA sequences encoding bovine and human acidic and basic FGF (acidic bFGF, acidic hFGF, basic bFGF, and basic hFGF). In other aspects, the invention relates to recombinant vectors bearing these DNA sequences, to host cells transformed with such vectors and harboring these DNA sequences, and to the recombinant proteins produced by these transformed cells. In other aspects, the invention relates to methods of producing these fibroblast growth factors using recombinant techniques.

BRIEF DESCRIPTION OF THE DRAWINGS

FIGS. 1-4 show the partial or complete DNA sequences encoding, and the deduced amino acid sequences of, acidic bFGF, acidic hFGF, basic bFGF, and basic hFGF.

FIG. 7 shows the DNA sequence of the bovine acidic FGF genomic probe 250/AluI.

FIG. 9 shows basic FGF probes 1097/1098.

MODES OF CARRYING OUT THE INVENTION

A. The Fibroblast Growth Factors

Figure 5:
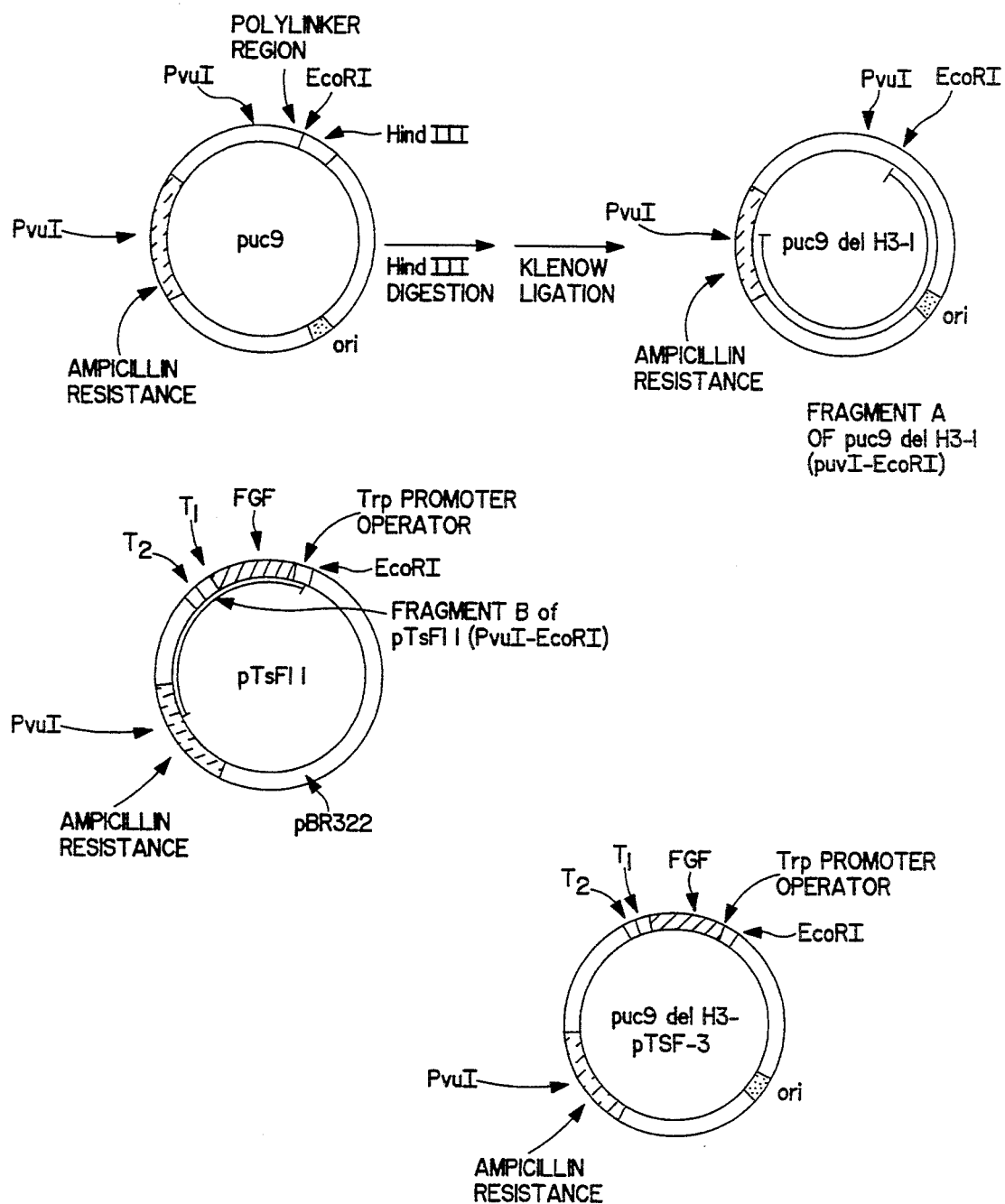
FIG. 5 shows the oligonucleotide probes 889/890, 891 and 853-856 designed from the acidic bFGF N-terminal sequence.

Two different bovine fibroblast growth factors have been purified to homogeneity by others and partially or completely sequenced. Both factors are capable of mitogenic activity in in vitro assays using cultured cells, such as bovine brain and adrenal cortex-derived capillary endothelial cells, human umbilical vein endothelial cells, bovine adrenal cortex cells, granulosa cells, and vascular smooth muscle cells. In vitro assays employing these cell cultures have been described by Gospodarowicz, D., et al, *J Cell Physiol* (1985) 122:323-332; and Gospodarowicz, D., et al, *J Cell Biol* (1983) 97:1677-1685. According to Gospodarowicz et al., *Journal of Cellular Physiology*, 122:323-332 (1985), the mitogenic activity of the column fractions and purified FGF samples was determined by using adult bovine aortic arch endothelial cells as target cells, as described in Gospodarowicz et al., "Clonal Growth of Bovine Endothelial Cells and Tissue Culture: Fibroblast Growth Factor as a Survival Agent," PNAS 73:4120-4124 (1976); and in Gospodarowicz et al., "Purification in High Yield of Brian Fibroblast Growth Factor by Preparative Isoelectric Focusing at pH 9.6, "*J. Biol. Chem.*, 257:12266-12278 (1982). Stock cultures, maintained in the presence of DMEM H16 supplemented with 10% calf serum, 50 μg/ml gentamicin, 0.25 μg/ml Fungizone, and brain FGF G-75 fraction, (100 ng/ml added every other day), were passaged weekly at a split ratio of 1 to 64.

For mitogenic assay, cell monolayers from stock plates were dissociated by exposure (2-3 min, 24° C.) to a solution containing 0.9% NaCl, 0.01M Na phosphate (PBS) (pH 7.4), 0.05% trypsin, and 0.02% EDTA (STV solution, Difco). When cells rounded up, they were resuspended in DMEM-H16 supplemented with 10% calf serum, and an aliquot of the cell suspension was counted in a Coulter counter. Cells were seeded at an initial density of $2 \times 10^4$ cells per 35-mm dish containing 2 ml of DMEM-H16 supplemented with 10% calf serum and antibiotics, as described above. Six hours later a set of triplicate plates was trypsinized and cells were counted to determine the plating efficiency. Ten-microliter aliquots of the appropriate dilution of each sample as indicated in the figure legends were then added to the dishes on day 0. After 4 days in culture, triplicate plates were trypsinized and cell densities were determined with a Coulter counter.

The mitogenic activity of pituitary FGF was also tested on bovine corneal endothelial cells, vascular smooth muscle, granulosa cells, adrenal cortex cells, human umbilical endothelial cell, and rabbit costal chrondrocyte cultures maintained as described in Gospodarowicz et al., "Effects of Fibroblast and Epidermal Growth Factors on Ovarian Cell Proliferation in vitro: I. Characterization of the Response of Granulosa Cells to FGF and EGF," *Endocrinology*, 100: 1108-1120 (1977); Gospodarowicz, et al., "Control of Bovine Adrenal Cortical Cell Proliferation by Fibroblast Growth Factor. Lack of Effect of Epidermal Growth Factor," *Endocrinology*, 100:1080-1089 (1977); Gospodarowicz, et al., "Stimulation of Corneal Endothelial Cell Proliferation in vitro by Fibroblast and Epidermal Growth Factor," *Exp. Eye Res.*, 25:75-89 (1977); Gospodarowicz, et al., "Factors Controlling the Proliferative Rate, Final Cell Density, and Life Span of Bovine Vascular Smooth Muscle Cells in Culture," *J. Cell Biol.* 89: 568-578 (1981); Gospodarowicz, et al., "Purification of Pituitary and Brain Fibroblast Growth Factors and Their Use in Cell Culture," *Methods in Molecular and Cell Biology*, Vol. 3 pp. 167-198 (1983); and Kato et al., "Effect of Extracellular Matrix Produced by Bovine Endothelial Cells on Proteoglycan Biosynthesis by Rabbit Costal Chondrocytes,"" *J. Cell Physiol.*, 120:359-363 (1984). Cells were seeded at an initial density of 2 or $4 \times 10^4$ cells per 35-mm dish. Assays where conducted as described for bovine vascular endothelial cells. Purified basic bFGF has been shown to be angiogenic in vivo in a chicken chorioallantoic membrane assay. (Gospodarowicz, D. in *Hormonal Proteins and Peptides* XII:205-230 (Academic Press).

Bovine pituitary basic FGF has been completely sequenced. The primary sequence contains 146 amino acids in agreement with the sequence deduced herein from the clone and is shown in FIG. 3. A higher molecular weight human basic FGF has been reported from the human hepatoma cell line, SK-Hep-1, by Sullivan, R. J., et al, *J Cell Biol* (1985) 101:108a. The human sequence determined herein from genomic and cDNA is shown in FIG. 4. From translation of the upstream sequence to an ATG start codon, both in DNA encoding the bovine and in DNA encoding the human protein shown in FIG. 3 and 4, respectively, it is likely that an additional form of each protein containing nine amino acids upstream of the first amino acid shown in these figures is also produced. Proteins having FGF activity in the above-mentioned in vitro assays and sharing a similar N-terminal sequence with the bovine pituitary basic FGF shown in FIG. 3 have also been isolated from bovine brain, adrenal gland, corpus luteum, retina, kidney, and from human placenta. The native protein obtained from certain of these tissues is heterogeneous—a second form missing the fifteen N-terminal amino acids retains activity. (Gospodarowicz, D. *Meth Enz* (1985) in press.) It is considered therefore, that bovine and human basic FGFs exist in three forms—those shown in FIGS. 3 and 4, longer forms containing nine amino acids at the N-terminus, and shorter forms lacking fifteen amino acids of the sequences shown. These FGFs are designated "basic" FGF, because they contain a high number of basic amino acid residues (lysine, arginine, histidine) and are therefore cations at neutral pH.

A protein is defined herein as basic FGF if it shows FGF activity in the foregoing assays, binds to heparin, is a cation at neutral pH, and reacts immunologically with antibodies prepared using a synthetic analog of the amino terminal sequence [tyr$^{10}$] FGF (1–10) conjugated to bovine serum albumin (if appropriate) or to other antibodies raised against bFGF or synthetic or native peptides thereof. See Baird, A., et al, *Regulatory Peptides* (1985) 10:309–317.

Acidic FGF has been isolated from bovine brain by others, and the first 34 amino acid residues determined. Subsequent to much of the work described below, the complete amino acid sequence for acidic bFGF was disclosed by Esch, et al, *Biochem Biophys Res Comm* (1985) in press. The acidic protein also has two known active forms, one having the 140 amino acid sequence beginning at the amino acid numbered "1" in FIG. 1, and a second shorter form corresponding to amino acids 7–140. The cloning herein of the genes for bovine and human acidic FGF has permitted additional amino acid sequences for acidic bFGF, and a partial sequence for acidic hFGF, to be deduced as shown in FIGS. 1 and 2. Both of these proteins may also occur in N-terminal extended forms. Translation of DNA upstream of the codon for the amino acid numbered "1" in FIGS. 1 and 2 to the ATG start codon (shown in parentheses in the Figures) represents the additional sequence of the extended protein. Therefore, like the basic FGF described above, the native protein may exist in three active forms, one truncated, one N-terminal extended, and the other containing the amino acid sequence beginning at the Phe residue numbered "1" in the figures. The primary structures of these proteins contain a disproportionate number of acidic amino acid residues, i.e., glutamic and aspartic acids and the proteins are therefore anions at neutral pH.

A protein is defined herein as acidic FGF if it shows FGF activity in in vitro assays, binds to heparin, is an anion at neutral pH, and is immunologically reactive with antibodies prepared against human or bovine acidic FGF or against synthetic or native peptides thereof.

Acidic FGF and basic FGF are thus used herein to designate the foregoing proteins or proteins having amino acid sequences substantially similar to those shown in FIGS. 1–4. Of course, these definitions are not restricted to the specific sequences shown, but include proteins which contain accidentally or deliberately induced alterations, such as deletions, additions, or exchanges of amino acid residues, so long as the biological activity, as measured by the foregoing in vitro and immunological assays, and respective anionic or cationic character at neutral pH does not change. Of course, modified forms may have slightly altered quantitative activity and specificity.

"Purified" or "pure" refers to material which is free from substances which normally accompany it as found in its native state. Thus "pure" acidic hFGF, for example, refers to acidic hFGF which does not contain materials normally associated with its in situ environment in human brain or pituitary. Of course, "pure" acidic hFGF may include materials in covalent association with it, such as glycoside residues.

"Operably linked" refers to a juxtaposition wherein the components are configured so as to perform their usual function. Thus, control sequences or promoters operably linked to a coding sequence are capable of effecting the expression of the coding sequence.

"Control sequence" refers to a DNA sequence or sequences which are capable, when properly ligated to a desired coding sequence, of effecting its expression in hosts compatible with such sequences. Such control sequences include at least promoters in both procaryotic and eucaryotic hosts, and optionally, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant FGF.

B. General Method

The invention provides DNAs encoding growth factor proteins which are useful in encouraging the healing of wounds and which further may be supplied in sufficiently pure amounts to permit the design of inhibitors specific to them. The purified growth factors are generally applied topically to the traumatized tissue in order to stimulate vascularization and healing. Appropriate substrates are burns, wounds, bone fractures, surgical abrasions such as those of plastic surgery, or others requiring repair. Because application of these factors accelerates healing, they also reduce the risk of infection.

Formulations of the recombinantly produced growth factors using available excipients and carriers are prepared according to standard methods known to those in the art. The proteins can be formulated as lotions, gels, as part of a controlled release system, or ointments with additional active ingredients, such as antibiotics, if desired. The invention provides practical quantities of pure FGF growth factors for use in direct application to wounds in these formulations.

Four specific endothelial growth factors are exemplified: bovine acidic and basic FGF, and their human counterparts. The acidic factors are considered to occur in three forms, one with the N-terminal sequence starting with "1" in FIGS. 1 and 2, the N-terminal extended forms which additionally contain the fifteen amino acids there shown in parentheses, and the truncated forms starting at residue 7. The basic factors seem also to occur in three forms. One form is the 146 amino acid sequence shown in FIGS. 3 and 4, a second is the shortened form beginning at amino acid 16 in these figures, and the third is the N-terminal extended form containing nine additional amino acids as shown in parentheses in these figures. The N-terminal extensions in both cases may represent "pro" sequences, however. It is also not clear whether the N-terminal methionine is processed off, remains intact, or is derivatized post-translation.

The general strategy whereby these illustrated sequences were obtained is as follows. The known N-terminal sequence of bovine acidic FGF was used to design a series of probes for use with a bovine genomic library ligated into phage. Phage recombinants which hybridized to the probes were isolated from the library and digested into smaller fragments suitable for cloning into M13 cloning vectors in order to obtain a "natural" probe. This resulted in an M13 probe containing a 250 bp sequence corresponding to a portion of the bovine acidic protein; this probe is central to recovering the complete coding sequences for the acidic forms of both bovine and human sources, as well as to obtaining the genes for the basic forms in these species.

Briefly, the fragments obtained by AluI digestion of a selected acidic bFGF gene cloned into phage were shotgun cloned into M13 and a 250 bp fragment which hybridized to appropriate probe DNA selected and sequenced. The above, designated 250/AluI, was transferred into pBR322 and was used to probe a bovine brain, hypothalamus or pituitary cDNA library (to obtain the complete acidic bFGF sequence uninterrupted by introns) and a human genomic library (to obtain the human acidic FGF genomic sequence). In addition, this same 250 bp fragment was used to design probes for the basic form, taking advantage of the available amino acid sequence information to alter the DNA to correspond to the basic rather than acidic form. The modified probe, thus designed on the basis of a comparison of the acidic bFGF N-terminal coding sequence and the basic bFGF amino acid sequence, was used to probe the same bovine pituitary cDNA library for the basic bFGF cDNA. The recovered bovine clone was then used to probe human genomic and cDNA libraries to recover the genomic sequence encoding human basic FGF-encoding DNA. For both acidic and basic FGF, the cDNA and genomic clones described hereinbelow are useful in probing DNA libraries prepared from various species to obtain the analogous coding sequences from these mammalian libraries. cDNA libraries prepared from various tissues such as pituitary, brain, hypothalamus, or kidney can also be screened in this manner.

The cloned genomic or cDNA sequences can be expressed in appropriate expression systems. cDNA sequences can be provided with appropriate controls suitable for any host, including bacteria, yeast, or eucaryotic cells. Genomic sequences containing introns can be expressed using eucaryotic control sequences and eucaryotic hosts which are capable of splicing the transcripts. Exemplary control sequence DNAs and hosts are given in paragraph C.1 below.

The recombinant FGF proteins thus produced are then purified in a manner similar to that utilized for purification of FGF from natural sources, but purification is considerably simpler, as the proteins form a much larger proportion of the starting material.

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

C.1 Hosts and Control Sequences

Both procaryotic and eucaryotic systems may be used to express the FGF encoding sequences; procaryotic hosts are, of course, the most convenient for cloning procedures. Procaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al *Nucleic Acids Res* (1980) 8:4057) and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the $2\mu$ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enz* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMTII (Karin, M., et al, *Nature* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

C.2. Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the $RbCl_2$ method described in Maniatis, et al, *Molecular Cloning: A Laboratory Manual* (1982) Cold Spring Harbor Press, p. 254 and Hanahan, D., *J Mol Biol* (1983) 166:557–580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Beggs, J. D., *Nature* (1978) 275:104–109 or of Hinnen, A., et al, *Proc Natl Acad Sci (USA)* (1978) 75:1929.

C.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth in C.1 above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizeable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles $\gamma32P$-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 μl volumes under the following standard conditions and temperatures: for example, 20 mM Tris-Cl pH 7.5, 10 mM $MgCl_2$, 10 mM DTT, 33 μg/ml BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per μg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al, *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

C.4. Verification of Construction

In the constructions set forth below, correct ligations for plasmid construction are confirmed by first transforming E. coli strain MC1061 obtained from Dr. M. Casadaban (Casadaban, M., et al, J Mol Biol (1980) 138:179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, Proc Natl Acad Sci (USA) (1969) 62:1159, optionally following chloramphenicol amplification (Clewell, D. B., J Bacteriol (1972) 110:667). Several mini DNA preps are commonly used, e.g., Holmes, D. S., et al, Anal Biochem (1981) 114:193-197 and Birnboim, H. C., et al, Nucleic Acids Res (1979) 7:1513-1523. The isolated DNA is analyzed by restriction and/or sequenced by the dideoxy nucleotide method of Sanger, F., et al, Proc Natl Acad Sci (USA) (1977) 74:5463 as further described by Messing, et al, Nucleic Acids Res (1981) 9:309, or by the method of Maxam, et al, Methods in Enzymology (1980) 65:499.

C.5. Hosts Exemplified

Host strains used in cloning and procaryotic expression herein are as follows:

For cloning and sequencing, and for expression of construction under control of most bacterial promoters, E. coli strains such as MC1061, DH1, RR1, C600hfl, K803, HB101, JA221, and JM101 were used.

D. Illustrative Procedure

The following examples are intended to illustrate but not to limit the invention. The DNA encoding the illustrated FGF sequences is obtained initially by screening a bovine genomic library and obtaining a pivotal probe, followed by retrieval of additional DNA. However, it would not be necessary to repeat this procedure, as the sequence of the pivotal probe is now known and could thus be constructed chemically in vitro. In addition, bacteriophage harboring the four illustrated sequences are deposited at the American Type Culture Collection.

EXAMPLE 1

Construction of the 250/AluI Probe: Preparation of Acidic bFGF Genomic DNA

A 250 bp AluI bovine genomic fragment was used to probe both human and bovine libraries in order to obtain complete coding sequences for the illustrated FGF proteins. This probe, designated 250/AluI, was obtained as follows.

The N-terminal amino acid sequence for residues 1-34 of bovine acidic FGF is known. Three long probes were prepared, based on codon choice (Anderson, S., et al, Proc Natl Acad Sci (USA) (1983) 80:6838-6842; Jaye, M., et al, Nucleic Acids Res (1983) 11:2325-2335) using an automatic synthesizer and a phosphoramidite coupling reagent. The sequences of these nucleotide probes are shown in FIG. 5. Probe 891 is a 48-mer corresponding to amino acids 1-16; probes 889 and 890 are 51-mers corresponding to amino acids 18-34 and are used as a 50—50 mixture of the two oligonucleotides which are identical except for the codon for arginine at position 24. The probes were used to screen a bovine genomic library obtained from Dr. Fritz Rottman, Case Western Reserve, which had been prepared as a partial MboI digest and was cloned into BamHI treated phage vector Charon 28 (Woychik, R. F., et al, Nucleic Acids Res (1982) 10:7197-7210).

Hybridization was conducted on denatured DNA replicated onto filters using a modification of the method described by Ullrich, A., et al, EMBO J (1984) 3:361-364; and the washing conditions were those of Wood, W. I., et al, Nature (1984) 312:330-337. Prehybridization/hybridization buffer contained 20% formamide, 5×Denhardt's solution (100×Denhardt's equals 2% bovine serum albumin, 2% polyvinyl pyrollidone; 2% Ficoll); 6×SSC (20×SSC equals 3M NaCl, 0.3M Na citrate); 50 mM sodium phosphate, pH 6.8; 100 μg/ml herring sperm DNA; hybridization buffer further included 10% dextran sulfate and about $10^5$-$10^6$ cpm/ml kinased probes 891 or 889/890. Prehybridization and hybridization were at 42° C. for 1 hr and 16 hr respectively. The filters were then washed 2×15 min with 1×SSC, 0.1% SDS at 22° C., followed by 1 ten minute wash in 1×SSC, 0.1% SDS at 55° C. After washing, the filters were exposed for 1 day using intensifying screens.

The screened bovine genomic library contained 50 phage out of $10^6$ recombinants which hybridized to both probes. These 50 phage were further screened with mixtures of probes 853-856. In this screen, prehybridization/hybridization buffer contained 6×SSC, 1×Denhardt's, 0.1% SDS, 0.05% Na pyrophosphate, and 100 μg/ml salmon sperm DNA; hybridization buffer further contained $10^5$-$10^6$ cpm/ml probe. Probes 853-856 are 4 pools of 16 sequences each of the 64 (total) 17-mers corresponding to amino acids 7-12, synthesized using the phosphotriester method. However, 46 of the 50 clones further hybridized to the shorter probes. This hybridization was performed at between 65° C. to 35° C. for 16 hr and the base composition independent washing method using tetramethyl ammonium chloride at 50° C. was used (Wood, W. I., Proc Natl Acad Sci (USA) (1985) 82:1585-1588).

Figure 6:
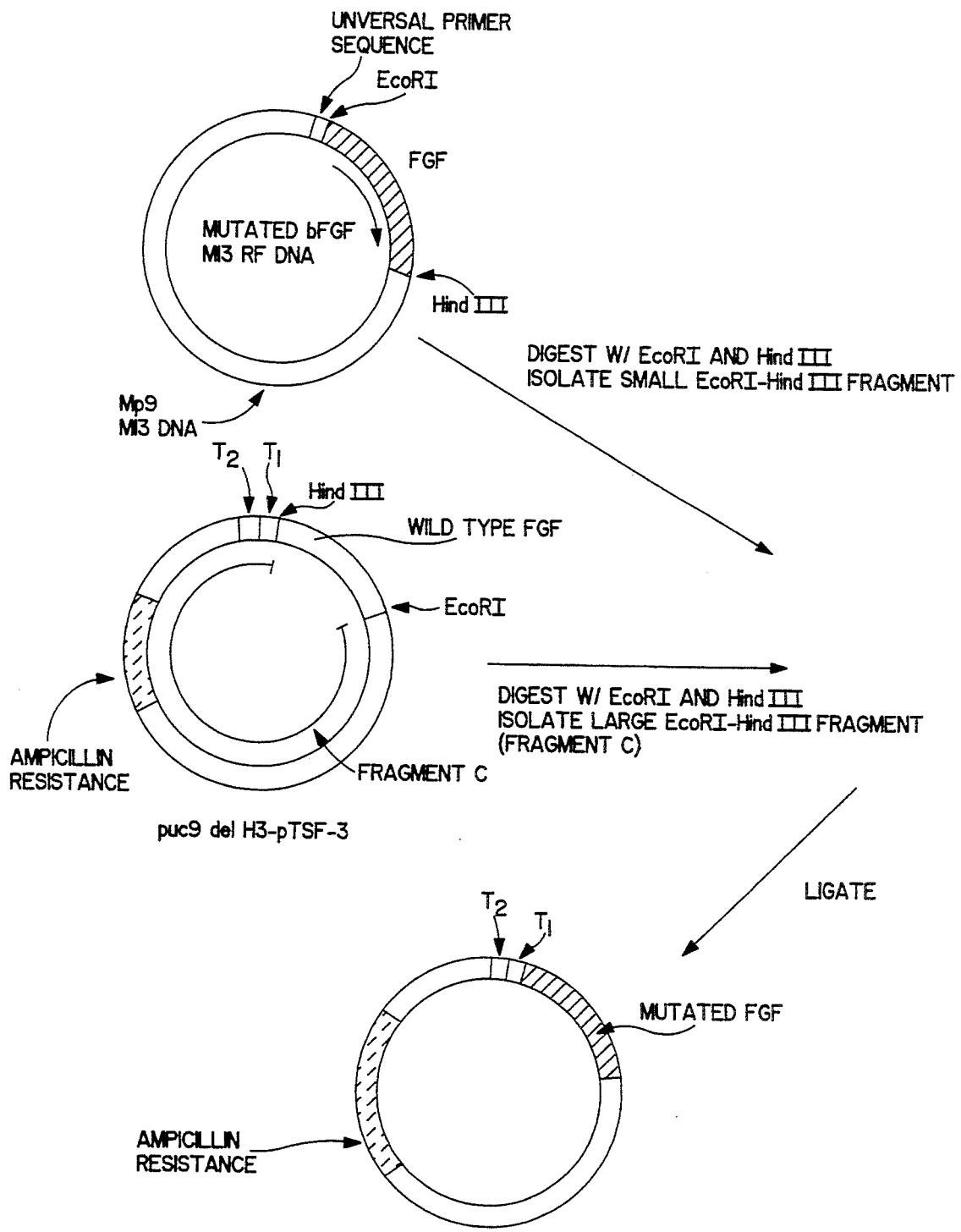
FIG. 6 gives restriction maps of the inserts for genomic acidic bFGF clones λBA2 and λBA3.

Two positively hybridizing phage were selected (λBA2 and λBA3) and the phage inserts were restriction mapped, as shown in FIG. 6, and partially sequenced as shown in FIG. 1. Comparison of the deduced amino acid sequence with that published for the N-terminal 34 residues of the bovine acidic FGF native protein confirms that these clones are correct. From the nature of the coding sequence it is apparent that amino acid residues 1-41 are encoded in these clones; immediately subsequent nucleotides appear to represent an intron. The length of this intron is, at present, uncertain, but it is believed that the complete acidic bFGF encoding sequence resides on these λBA2 and λBA3 DNAs. However any additional DNA required to obtain the complete coding sequences for this protein can be obtained from the same gene library using the λBA2 or λBA3 in "walking" techniques. The codons preceding the N-terminal residue are believed to encode a fifteen amino acid prosequence, or, as discussed above, an alternative form of the native protein extended by fifteen amino acids at the N-terminus (or by fourteen if the N-terminal methionine is cleaved) as compared to isolated form.

To prepare the 250/AluI and shotgun cloned into M13 (Messing, J., et al, *Gene* (1982) 19:269–276). The M13 plaques were hybridized in duplicate with 853–856 and 889/890. Phage hybridizing to both probes were sequenced. The resulting 250 bp AluI probe is shown in FIG. 7 along with the corresponding deduced amino acid sequence; its location on the λBA2 and λBA3 inserts of FIG. 6 corresponds to the site of probes 889/890 and 891. The 250/AluI probe corresponds to the N-terminal portion of the acidic bFGF protein.

EXAMPLE 2

Recovery of Acidic bFGF cDNA

The 250/AluI probe is used to retrieve the cDNA sequence encoding acidic bFGF. A cDNA library is obtained from bovine pituitary, brain, or hypothalamus mRNA using the λgt10 vector of Huynh, V. T., et al, *DNA Cloning Techniques: A Practical Approach* (IRL Press, Oxford, 1984). The resulting hybridizing clones permit recovery of the entire sequence encoding acidic bFGF.

Comparable cDNA libraries constructed using the analogous mRNA from other mammalian species is probed with the 250/AluI probe to obtain, for example, rat, ovine, bovine, feline, canine, equine, or porcine basic FGF.

EXAMPLE 3

Preparation of Acidic hFGF Genomic DNA

Figure 8:
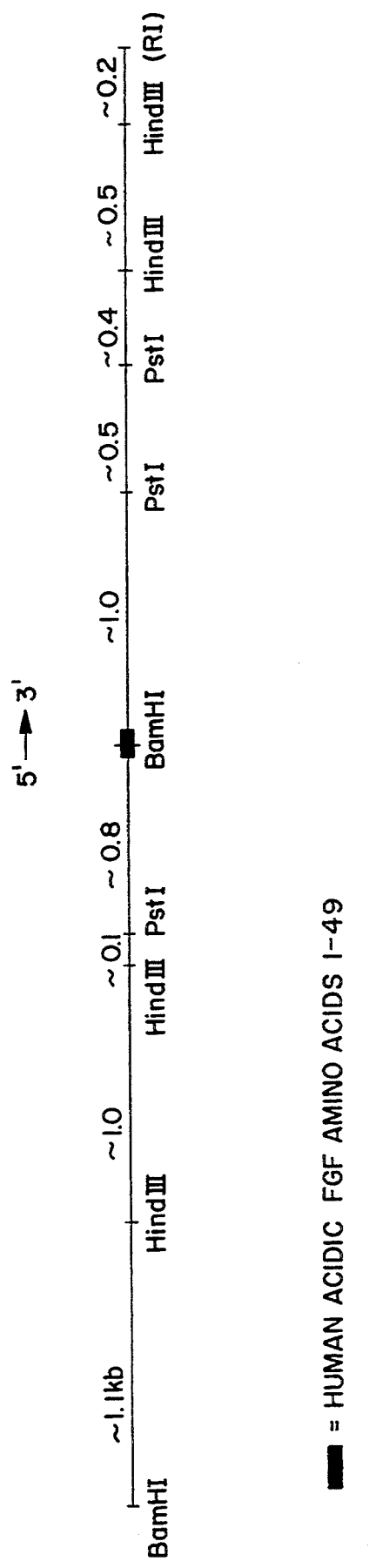
FIG. 8 is a restriction map of the insert in acidic hFGF genomic clone HAG-9.1.

A human fetal liver genomic library in Charon 4A (Lawn, R. M., et al, *Cell* (1978) 15:1157–1174) was used as a source of the human sequences. The library was probed with the 250/AluI probe prepared in Example 1. The conditions of prehybridization/hybridization were the same as those for the 889/890 and 891 probes of Example 1, except that 40% formamide was used. Hybridization was at 42° C. for 16 hr. The filters were then washed at room temperature with 1×SSC, 0.1% SDS, and then for 2×15 min at 50° C. with the same buffer. Positively hybridizing clones were cultured, and one, designated λHAG-9.1, contained the desired acidic hFGF sequences. A partial restriction map of this clone is shown in FIG. 8; nucleotide and amino acid sequence information is shown in FIG. 2. The nucleotide sequence encoding amino acids 1–41 can be identified; this sequence, as in the genomic acidic bFGF, appears to be followed by an intron. The acidic hFGF and bFGF amino acid sequences differ at positions 5, 21, and 35.

Human acidic FGF-encoding DNA also contains 15 codons preceding the N-terminus of the corresponding bovine isolated protein, which encode an amino acid sequence highly homologous to the N-terminal extension of the bovine protein. The translated sequence is shown in parentheses in FIG. 2. There are nucleotide substitutions in codons -3, -6, -9, and -12, which are silent in the translated protein. A nucleotide change in codon -10 results in the Thr residue of the bovine protein being an Ile residue in the human protein. As for the bovine acidic FGF, this N-terminal extension may represent a prosequence or an alternative form of the native, active protein, either containing a fourteen or fifteen amino acid N-terminal extension depending on the fate of the methionine.

EXAMPLE 4

Preparation of Acidic hFGF cDNA

A cDNA library prepared from human pituitary, brain or hypothalamus mRNA by the method of Huynh, as described for the bovine mRNA in Example 2, is probed with the 250/AluI probe under the conditions described in Example 3 to obtain the cDNA encoding acidic hFGF.

EXAMPLE 5

Retrieval of Basic bFGF Genomic and cDNA

The 250/AluI probe was then used to design appropriate probes to obtain the corresponding basic bFGF sequences. Advantage was taken of the finding of Esch, F., et al (supra) that amino acids 4–29 of acidic bFGF align with amino acids 13–38 of the basic bFGF sequence. Probes were designed based on the basic bFGF residues 18–36 and acidic bFGF residues 9–27, which regions are homologous at 14 of the 19 amino acids.

Probes 1097 and 1098, 40-mers designed to encode this region, were prepared using the phosphoramidite method on an automatic synthesizer. The probes are shown in FIG. 9; they overlap in the amino acid 23–31 region of the basic sequence. In designing the probes, the 250/AluI sequence was used where the amino acid sequence was the same, and where different, minimum nucleotide differences in order to effect the required change in encoded sequence were incorporated.

The bovine pituitary cDNA library obtained by the method of Huynh, V. T., as set forth in Example 2, was screened with 1098. Correct conditions for hybridization were determined using genomic DNA (Example 1) for Southern blot as follows:

It was, of course, expected that the 1097 and 1098 probes would cross-hybridize with acidic FGF encoding DNA under low stringency conditions. Southern blot analysis showed that genomic sequences known to encode acidic bFGF which hybridized to 1097 and 1098 at 55° C. wash temperatures failed to hybridize at 65° C. (Prehybridization/hybridization buffer and conditions were as for 889/890 and 891 probes in Example 1.) Therefore, a wash temperature of 65° C. was chosen. At this temperature, a 10 kb fragment in an EcoRI digest and a 3.4 kb fragment in a PstI digest hybridized to probes 1097 and 1098.

Figure 10:
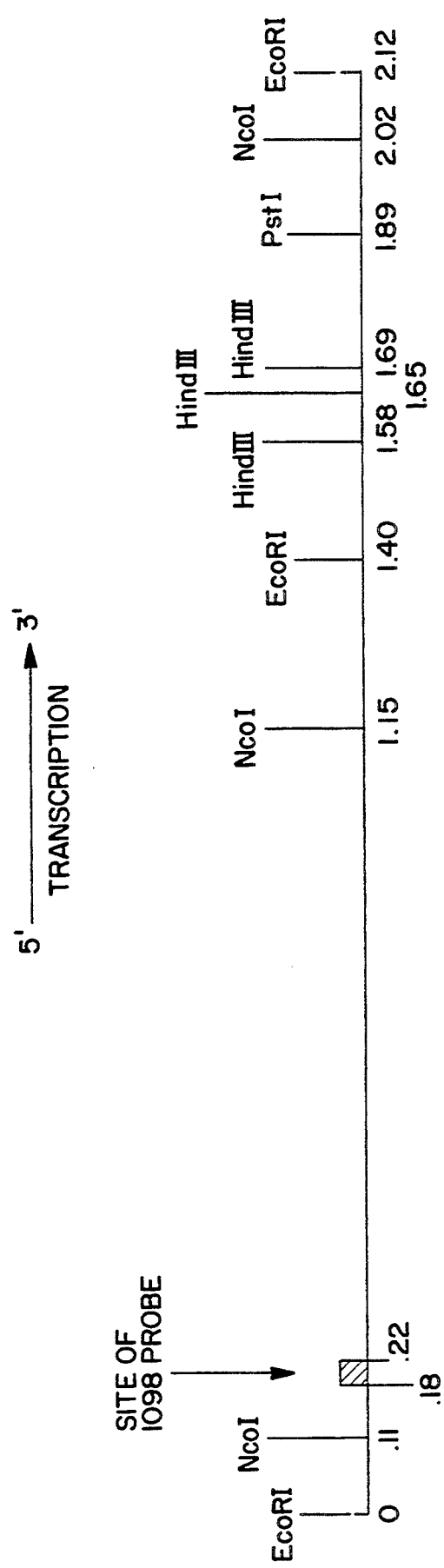
FIG. 10 is a restriction map of the basic bFGF cDNA clone λBB2.
Figure 6:
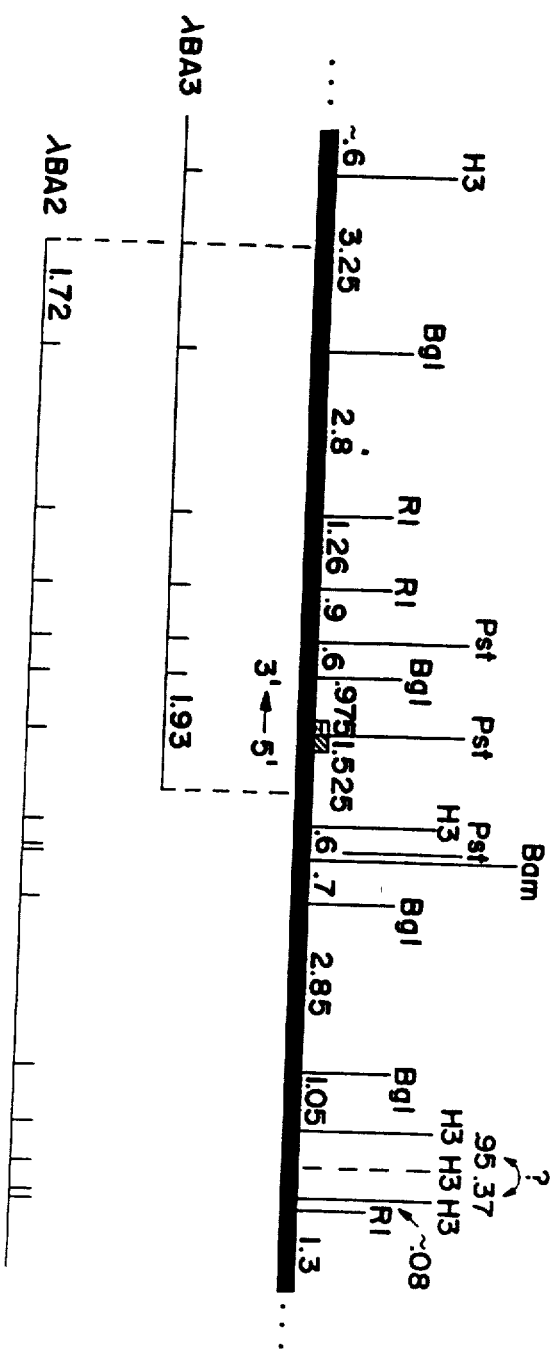

When the cDNA library was probed as above using a 65° C. wash temperature, a single clone designated λBB2, representing a 2.1 kb cDNA with EcoRI linkers, was recovered. A restriction map of this phage is shown in FIG. 10. Subfragments of the insert in λBB2 were transferred to M13 for sequencing and a 1.4 kb EcoRI-digested subfragment was shown to encode amino acids 1–146 (the complete sequence) of bovine basic FGF. The sequence upstream from the N-terminal codon is believed to encode either a nine amino acid prosequence or an N-terminal extended form of the native protein which retains activity. The N-terminal extension may contain only eight residues, of course, depending on whether the methionine is cleaved during post-translational processing. The portion of this subfragment encoding basic bFGF is shown in FIG. 3; amino acid numbering starting at position 1 corresponds to the N-terminus of the isolated protein. The upstream nine codons are translated in parentheses. The possibility that this extension represents an integral part of the native active protein is suggested by the higher MW form of the human basic FGF prepared from hepatoma cells by Sullivan, et al (supra).

The 1.4 kb subfragment is then nick translated and used to screen a bovine genomic library constructed in a manner similar to that of Example 1 for the basic bFGF genomic sequences.

The 1.4 kb basic bFGF-encoding cDNA fragment is also used to probe alternate mammalian cDNA libraries, such as those from rat, pig, or bovine, feline, canine, equine or murine sources to obtain the basic FGF encoding sequences from these species.

EXAMPLE 6

Preparation of Human Basic FGF Genomic and cDNA

A λgt10 cDNA library prepared from human kidney mRNA was also probed using the 1.4 kb bovine basic subfragment. Prehybridization/hybridization buffer contained 40% formamide, 5 mM Na phosphate, pH 6.5, 5×Denhardt's, 5×SSC, and 50 µg/ml herring sperm DNA; hybridization buffer also included 10% dextran sulfate and $10^4$–$10^5$ cpm/ml probe. Three clones were isolated, and one selected for characterization. This clone, designated λKB7, contained an approximately 1.4 kb EcoRI fragment which was partially sequenced to yield the data shown in FIG. 4, along with the deduced amino acid sequence. The sequenced coding region permits deduction of amino acids 1–50 shown in the Figure; the continuing sequence immediately downstream appears to represent the cDNA copy of an unspliced mRNA, indicating that an intron occurs in the basic FGF gene in a homologous position to the intron after amino acid 41 in the bovine and human acidic FGF genes. The λKB7 clone also provides upstream DNA encoding the nine amino acid N-terminal extension shown.

Additional genomic and cDNA libraries were screened using the same 1.4 kb basic bFGF-encoding fragment under precisely the same hybridization conditions as those employed for the human kidney λgt10 library above. Four additional clones were obtained, which between them encode the entire 146 amino acid protein corresponding to the isolated basic bFGF, as shown in FIG. 4. Nine upstream codons included in λKB7 above translate into a sequence having complete homology with the translated upstream codons in the bovine basic FGF clone, although there is a silent nucleotide substitution in codon −8. This translated N-terminal extension is shown in parentheses in FIG. 4; and, as above, may represent a prosequence or the additional amino acids of an N-terminal extended active protein.

In more detail, two positively hybridizing clones from a human genomic library in λ Charon 4A, prepared as described by Lawn, R. M., et al (supra) were designated λMG4 and λMG10. λMG4 encodes amino acids 1–50; λMG10 encodes amino acids 86–146, representing the third of three exons contained in the mature protein-encoding region of the gene. (The location of exon/intron boundaries was determined by homology to the bovine sequence.) A slightly different genomic library in λ Charon 28, obtained from E. Fritsch, yielded λHT1 which contains the second mature protein exon, encoding amino acids 51–85. Finally, λHFL1, a cDNA clone obtained from a human fetal liver library prepared in λgt10 as described above, encodes amino acids 56–146, confirming the location of the relevant intron/exon junction.

There are only two amino acid differences between basic bFGF and hFGF, at position 112, where the bovine protein has Ser and the human protein has Thr, and at position 128, where the bovine protein has Pro and the human has Ser. These differences are the result of a single nucleotide difference in each case; therefore bovine cDNA may conveniently be modified by site directed mutagenesis as described below to encode the human protein.

EXAMPLE 7

Construction of Expression Vectors and Expression of FGF

The cDNA clones encoding FGF are most conveniently used to produce the recombinant proteins in a variety of hosts, as set forth in C.1 above. However, expression in mammalian systems is favored as the host is capable of post translational processing analogous to that experienced by the natively produced protein, and either cDNA or genomic sequences may be used, as the host is also capable of processing introns.

A full length cDNA or genomic FGF encoding clone is prepared for insertion into a host vector, illustrated by but not limited to those described below. (The full length cDNA encoding bovine basic FGF is converted to a cDNA encoding human FGF using the standard site directed mutagenesis procedure described above in C.3. For the Ser to Thr conversion at position 112, the 16-mer primer 5'-GAAATACACCAGTTGG-3' is used; for the Pro to Ser conversion at position 128, the 17-mer primer 5'-ACTTGGATCCAAAACAG-3' is employed.)

To construct the vectors, the cloned insert is excised with EcoRI (by partial digestion if the insert itself contains EcoRI sites), or other appropriate enzyme, provided with EcoRI linkers if necessary, and then inserted into the host vector pHS1 as described below.

Construction of pHS1, the Host Vector

The plasmid pHS1 is suitable for expression of inserted DNA in mammalian hosts. It contains 840 bp of the hMT-II sequence from p84H (Karin, M., et al, Nature (1982) 299: 297–802) which spans from the HindIII site at position −765 of the hMT-II gene to the BamHI cleavage site at base +70. To construct pHS1, plasmid p84H was digested to completion with BamHI, treated with exonuclease BAL-31 to remove terminal nucleotides, and then digested with HindIII. The desired 840 bp fragment was ligated into pUC8 (Vieira, J., et al, Gene (1982) 19: 259–268) which had been opened with HindIII and HincII digestion. The ligation mixture was used to transform E. coli HB101 to $Amp^R$, and one candidate plasmid, designated pHS1, was isolated and sequenced by dideoxy sequencing. pHS1 contains the hMT-II control sequences upstream of a polylinker containing convenient restriction sites.

Construction of Expression Vectors

The FGF encoding fragments, prepared as above, are ligated into EcoRI digested pHS1 and the ligation mixture used to transform E. coli MC1061 to $Amp^R$. Successful transformants are screened by restriction analysis, and a strain containing the desired plasmid, pMT-FGF is further propagated to prepare quantities of plasmid DNA.

Production of FGF by Mammalian Recombinants

Chinese hamster ovary (CHO)-K1 cells are grown on medium composed of a 1:1 mixture of F12 medium and DME medium with 12% fetal calf serum. The competent cells are co-transformed with pMT-FGF and pSV2:NEO (Southern, P., et al, *J Mol Appl Genet* (1982) 1: 327–341). pSV2:NEO contains a functional gene conferring resistance to the neomycin analog G418. In the transformation, 500 ng of pSV2-NEO and 5 μg of pMT-FGF are applied to a 16 mm dish of cells in a calcium phosphate-DNA co-precipitate according to the protocol of Wigler, M., et al, *Cell* (1979) 16: 777–785, with the inclusion of a two minute "shock" with 15% glycerol after four hours of exposure to the DNA. A day later, the cells are subjected to 1 mg/ml G418 to provide a pool of G418-resistant colonies, which are assayed for FGF production and then cloned out.

Successful transformants, also having a stable inheritance of pMT-FGF, are plated at low density for purification of clonal isolates. Small amounts of these isolates are grown in multi-well plates after exposure to $10^{-4}$M zinc chloride for convenient assay of FGF production. FGF determinations are made by standard ELISA or radio-immunoassays against the antisera prepared against the appropriate FGF protein using standard methods. Clonal isolates which produce large amounts of the desired FGF are selected.

The cells, which have been shown to produce FGF under suitable conditions, are seeded at 1/10 confluency in basal medium supplemented with 10% fetal calf serum, incubated overnight, and then induced for FGF production by addition of zinc chloride in the concentration range of $1\times10^{-4}$M to $3\times10^{-4}$M. FGF levels rise for 7–10 days, under optimal inducing conditions, $2\times10^{-4}$M $ZnCl_2$.

If desired, the FGF secreted into the medium can be purified according to the procedures set forth above for the native protein, or by other standard methods known in the art.

EXAMPLE 8

Bacterial Expression of FGF

The cDNA sequences encoding FGF, which are uninterrupted by introns, are also expressible in bacterial systems. A convenient host vector for expression is pKT52, which contains the "trc" promoter, followed by an ATG start codon. The construction of pKT52 is described in U.S. Ser. Nos. 616,488 and 622,639, assigned to the same assignee, and incorporated herein by reference. Briefly, the "trc" promoter contains the upstream portions of the trp promoter and the downstream, operator-containing, regions of the lac promoter and was originally prepared from two readily available plasmids containing these promoters. To construct the trc promoter as a BamHI/HindIII cassette, an intermediate plasmid pKK10-0 was prepared containing the hybrid promoter.

To prepare pKK10-0, pEA300 (Amman, E., et al, *Gene* (1983) 25:167–178) was digested with PvuII and ClaI, filled in using dCTP only in the presence of DNA polymerase (Klenow), followed by digestion with mungbean nuclease, and the large vector fragment isolated. This vector fragment contains the upstream portions of the trp promoter. The fragment was ligated with a 55 bp blunt-ended HpaII/PvuII digest excised from pGL101 (Lauer, G., et al, *J Mol Appl Genet* (1981) 1:139–147), which was prepared by digesting pGL101 with PvuII and HpaII followed by repair in the presence of dGTP and labeled dCTP. This fragment contains the lac operator region. The ligation product of these two blunt-end fragments was pKK10-0.

A BamHI site was inserted into pKK10-0 upstream of the trp/lac (trc) promoter/operator by digestion with EcoRI, filling in with Klenow, and insertion of the BamHI linker 5'-CCGGATCCGG-3'. The resulting plasmid, pKK10-1 was digested with PvuII, and ligated to the NcoI linker, 5'-ACCATGGT-3', digested with NcoI, filled in, and then ligated to a double-stranded linker containing PstI and HindIII sites provided as two complementary oligonucleotides, 5'-GCTGCAGC-CAAGCTTGG-3' and its complement. The ligation mixture was used to transform *E. coli* to $Amp^R$. The isolated plasmid DNA was digested with BamHI and HindIII, and the small BamHI/HindIII fragment obtained on electrophoresis contains the trc promoter.

To complete pKT52, the BamHI/HindIII fragment containing the trc promoter was ligated into the large fragment obtained from BamHI/HindIII digestion of pKK10-2 (Brosius, J., *Gene* (1984) 27:161–172) which contains the $Amp^R$ gene and the origin of replication. The resulting plasmid, pKK233-1 was digested to completion with PvuI and then partially with BglI and ligated with the 360 bp PvuI/BglI fragment containing the corresponding portion of the ampicillin resistance gene but lacking a PstI site from pUC8. The ligation mixture was used to transform *E. coli* and transformants were screened for the presence of only one PstI site next to the trc promoter. The correct construction, pKK233-2, was digested with EcoRI and PvuII, filled in with dATP and dTTP, and religated to obtain the correct construction pKT52.

pKT52 contains the desired trc promoter, a downstream ATG start codon, and downstream NcoI, PstI and HindIII sites.

For construction of expression vectors, the FGF-encoding cDNA is obtained by excising with EcoRI or other appropriate enzyme digestion and isolating and, if necessary, modifying the appropriate fragment. The 3' end is prepared for insertion into pKT52 by cutting downstream of the termination codon at any convenient restriction site and supplying PstI or HindIII linkers. The 5' end is prepared by cutting at a site inside the coding sequence and supplying the missing codons and an NcoI site using a synthetic DNA, or by providing an appropriately located NcoI site by mutagenesis. The resulting NcoI/HindIII or NcoI/PstI fragment is then ligated into NcoI/HindIII-digested pKT52 or NcoI/PstI digested pKT52 to provide the FGF-encoding cDNA in reading frame with the ATG start codon.

For bacterial expression, the resulting expression vectors are used to transform *E. coli* MC1061 or other appropriate host cells to $Amp^R$, and the transformed cells are then grown on M9 medium containing 1 mM IPTG for 3–5 hr to an O.D. of 0.2–0.5. (IPTG is a standard inducer for control sequences regulated by the lac operator.) The cells are then harvested, lysed by sonication or treatment with 5% trichloroacetic acid, and the cell extracts assayed for the desired FGF. FGF can be purified from the extracts by methods used for the native protein or by other procedures known in the art.

EXAMPLE 9

Activity of FGF in Promoting Wound Healing

FGF activity in promoting wound healing was assayed using native basic FGF purified from bovine pituitaries by the method of Gospodarowicz et al as a control (*Proc Natl Acad Sci* (USA) (1984) 81:6963–6967). The control bFGF to be assayed was applied to the subcutaneous implantation of polyvinyl alcohol sponges in rats according to the procedure of Davidson, J. M., et al, *J.C.B.* (1985) 100:1219–1227. In the alternative, Gortex hollow fibers may also be used (Goodson, W. H., et al, *J Surg Res* (1982) 33:394–401).

In the standard procedure, a total of four rats received two identically treated sponges each. The sponges were either not treated, treated with heparin sepharose beads, treated with FGF bound to heparin sepharose beads using 5 μg FGF per sponge; or treated with 5 μg FGF in solution. The sponges were removed after 6 days and examined histologically for granulation tissue, which is indicative of wound healing.

Sponges which contained FGF showed a higher amount of granulation, which was centered around the heparin sepharose beads in the case of the sponges where the FGF was supplied bound to these beads.

Similar results are observed whether the FGF is from native or recombinant sources and whether the FGF is basic or acidic.

On or before 9 Sep. 1985, Applicant deposited with the American Type Culture Collection (ATCC), Rockville, Md., USA, the λ phage λBA2, λBA3, λHAG-9.1, λBB2, and λKB-7 which were assigned ATCC accession numbers 40195, 40194, 40197, 40196, and 40198, respectively. These deposits were made under conditions as provided under ATCC's agreement for Culture Deposit for Patent Purposes, which assures that these deposits will be made available to the U.S. Commissioner of Patents and Trademarks pursuant to 35 USC 122 and 37 CFR 1.14, and will be made available to the public upon issue of a U.S. patent which requires these deposits to be maintained. Availability of the deposited strains is not to be construed as a license to practice the invention in contravention of the rights granted under the authority of any government in accordance with its patent laws.

We claim:

1. A recombinant DNA sequence encoding human basic fibroblast growth factor.

2. The DNA of claim 1 which hybridizes to a 1.4 kb EcoRI subfragment of λBB2 under conditions suitable for probing cDNA libraries.

3. The DNA of claim 2 which encodes a protein comprising the human fibroblast growth factor shown as amino acids 16–146 of FIG. 4.

4. A recombinant DNA expression vector which comprises DNA encoding human basic fibroblast growth factor, wherein the vector expresses the DNA encoding human basic fibroblast growth factor in a microorganism or cell culture harboring said vector.

5. The vector of claim 4 wherein, upon expression, the DNA encoding human basic fibroblast growth factor protein produces a human fibroblast growth factor protein which has the amino acid sequence numbered 1–146 in FIG. 4.

6. The vector of claim 4 wherein, upon expression, the DNA encoding human basic fibroblast growth factor protein produces a human fibroblast growth factor protein which has the amino acid sequence numbered 16–146 in FIG. 4.

7. The vector of claim 4 wherein, upon expression, the DNA encoding human basic fibroblast growth factor protein produces a human fibroblast growth factor protein which has the amino acid sequence numbered (−9) or (−8)–146 in FIG. 4.

8. The vector of claim 4 wherein the DNA encoding human basic fibroblast growth factor has a DNA sequence which is the reverse transcript of the human fibroblast growth factor encoding portion of an mRNA natively encoding said human basic fibroblast growth factor.

9. The vector of claim 4 wherein the DNA encoding human fibroblast growth factor is uninterrupted by introns.

10. A recombinant host cell transformed with the vector of claim 4.

11. A microorganism transformed with the vector of claim 4, said microorganism being capable of expressing the DNA encoding human basic fibroblast growth factor.

12. The microorganism of claim 11 which is *E. coli*.

13. The microorganism of claim 11 wherein the human fibroblast growth factor comprises the amino acid sequence numbered 16–146 in FIG. 4.

14. A cell culture which expresses DNA encoding human basic fibroblast growth factor, obtained by transforming a cell line with the vector of claim 4.

15. The cell culture of claim 14 wherein the cell line is a mammalian cell line.

16. The cell culture of claim 15 wherein the cell line is a Chinese hamster ovary cell line.

17. The cell culture of claim 14 wherein the human fibroblast growth factor comprises the amino acid sequence numbered 16–146 in FIG. 4.

* * * * *

UNITED STATES PATENT AND TRADEMARK OFFICE
CERTIFICATE OF CORRECTION

PATENT NO. : 5,439,818
DATED : August 8, 1995
INVENTOR(S) : John C. Fiddes, et. al.

It is certified that error appears in the above-identified patent and that said Letters Patent is hereby corrected as shown below:

Drawings:

Delete "Figures 1-6", and insert the attached --Figures 1-6 as shown on the attached sheets--.

Signed and Sealed this

Thirteenth Day of August, 1996

*Attest:*

BRUCE LEHMAN

*Attesting Officer*     *Commissioner of Patents and Trademarks*

```
                                                                   AGC
TGC TGA GCC ATG GCT GAA GGA GAA ACC ACG ACC TTC ACG GCC CTG ACT GAG AAG
        (Met Ala Glu Gly Glu Thr Thr Thr Phe Thr Ala Leu Thr Glu Lys)
            -15                                                    -1

TTT AAC CTG CCT CTA GGC AAT TAC AAG AAG CCC AAG CTC CTC TAC TGC AGC AAC
Phe Asn Leu Pro Leu Gly Asn Tyr Lys Lys Pro Lys Leu Leu Tyr Cys Ser Asn
 1                              10

GGG GGC TAC TTC CTG AGA ATC CTC CCA GAT GGC ACA GTG GAT GGG ACG AAG GAC
Gly Gly Tyr Phe Leu Arg Ile Leu Pro Asp Gly Thr Val Asp Gly Thr Lys Asp
    20                                  30

AGG AGC GAC CAG CAC A GTAAGCACCCATCTCACATTTCTGGTATCTTCCTTACTCAGGGACAGGA
Arg Ser Asp Gln His
         40

GAAGGGAGAATAGGGAGAATAGCTAAGGGCT
```

FIG. 1

```
                                                                     T
GCT GAG GCC ATG GCT GAA GGG GAA ATC ACC ACC TTC ACA GCC CTG ACC GAG AAG
        (Met Ala Glu Gly Glu Ile Thr Thr Phe Thr Ala Leu Thr Glu Lys)
            -15                                                    -1

TTT AAT CTG CCT CCA GGG AAT TAC AAG AAG CCC AAA CTC CTC TAC TGT AGC AAC
Phe Asn Leu Pro Pro Gly Asn Tyr Lys Lys Pro Lys Leu Leu Tyr Cys Ser Asn
 1                              10

GGG GGC CAC TTC CTG AGG ATC CTT CCG GAT GGC ACA GTG GAT GGG ACA AGG GAC
Gly Gly His Phe Leu Arg Ile Leu Pro Asp Gly Thr Val Asp Gly Thr Arg Asp
    20                                  30

AGG AGC GAC CAG CAC A GTAAGCCCATCTCTATGGC
Arg Ser Asp Gln His
         40
```

FIG. 2

```
                                        ATG GCC GCC GGG AGC ATC ACC ACG CTG
                                       (Met Ala Ala Gly Ser Ile Thr Thr Leu)
                                        -9                                -1

CCA GCC CTG CCG GAG GAC GGC GGC AGC GGC GCT TTC CCG CCG GGC CAC
Pro Ala Leu Pro Glu Asp Gly Gly Ser Gly Ala Phe Pro Pro Gly His
 1                              10

TTC AAG GAC CCC AAG CGG CTG TAC TGC AAG AAC GGG GGC TTC TTC CTG
Phe Lys Asp Pro Lys Arg Leu Tyr Cys Lys Asn Gly Gly Phe Phe Leu
         20                                          30

CGC ATC CAC CCC GAC GGC CGA GTG GAC GGG GTC CGC GAG AAG AGC GAC
Arg Ile His Pro Asp Gly Arg Val Asp Gly Val Arg Glu Lys Ser Asp
                     40

CCA CAC ATC AAA CTA CAA CTT CAA GCA GAA GAG AGA GGG GTT GTG TCT
Pro His Ile Lys Leu Gln Leu Gln Ala Glu Glu Arg Gly Val Val Ser
 50                                              60

ATC AAA GGA GTG TGT GCA AAC CGT TAC CTT GCT ATG AAA GAA GAT GGA
Ile Lys Gly Val Cys Ala Asn Arg Tyr Leu Ala Met Lys Glu Asp Gly
                 70                                              80

AGA TTA CTA GCT TCT AAA TGT GTT ACA GAC GAG TGT TTC TTT TTT GAA
Arg Leu Leu Ala Ser Lys Cys Val Thr Asp Glu Cys Phe Phe Phe Glu
                                     90

CGA TTG GAG TCT AAT AAC TAC AAT ACT TAC CGG TCA AGG AAA TAC TCC
Arg Leu Glu Ser Asn Asn Tyr Asn Thr Tyr Arg Ser Arg Lys Tyr Ser
             100                                         110

AGT TGG TAT GTG GCA CTG AAA CGA ACT GGG CAG TAT AAA CTT GGA CCC
Ser Trp Tyr Val Ala Leu Lys Arg Thr Gly Gln Tyr Lys Leu Gly Pro
                         120

AAA ACA GGA CCT GGG CAG AAA GCT ATA CTT TTT CTT CCA ATG TCT GCT
Lys Thr Gly Pro Gly Gln Lys Ala Ile Leu Phe Leu Pro Met Ser Ala
 130                                             140

AAG AGC TGA TCT TAA
Lys Ser Ter     Ter
 146
```

FIG. 3

```
                                    ATG GCA GCC GGG AGC ATC ACC ACG CTG
                                   (Met Ala Ala Gly Ser Ile Thr Thr Leu)
                                    -9                                -1

CCC GCC TTG CCC GAG GAT GGC GGC AGC GGC GCC TTC CCG CCC GGC CAC
Pro Ala Leu Pro Glu Asp Gly Gly Ser Gly Ala Phe Pro Pro Gly His
 1                              10

TTC AAG GAC CCC AAG CGG CTG TAC TGC AAA AAC GGG GGC TTC TTC CTG
Phe Lys Asp Pro Lys Arg Leu Tyr Cys Lys Asn Gly Gly Phe Phe Leu
             20                                      30

CGC ATC CAC CCC GAC GGC CGA GTT GAC GGG GTC CGG GAG AAG AGC GAC
Arg Ile His Pro Asp Gly Arg Val Asp Gly Val Arg Glu Lys Ser Asp
                         40

CCT CAC ATC AAG CTA CAA CTT CAA GCA GAA GAG AGA GGA GTT GTG TCT
Pro His Ile Lys Leu Gln Leu Gln Ala Glu Glu Arg Gly Val Val Ser
 50                                          60

ATC AAA GGA GTG TGT GCT AAC CGT TAC CTG GCT ATG AAG GAA GAT GGA
Ile Lys Gly Val Cys Ala Asn Arg Tyr Leu Ala Met Lys Glu Asp Gly
                     70                                       80

AGA TTA CTG GCT TCT AAA TGT GTT ACG GAT GAG TGT TTC TTT TTT GAA
Arg Leu Leu Ala Ser Lys Cys Val Thr Asp Glu Cys Phe Phe Phe Glu
                                 90

CGA TTG GAA TCT AAT AAC TAC AAT ACT TAC CGG TCA AGG AAA TAC ACC
Arg Leu Glu Ser Asn Asn Tyr Asn Thr Tyr Arg Ser Arg Lys Tyr Thr
             100                                     110

AGT TGG TAT GTG GCA TTG AAA CGA ACT GGG CAG TAT AAA CTT GGA TCC
Ser Trp Tyr Val Ala Leu Lys Arg Thr Gly Gln Tyr Lys Leu Gly Ser
                         120

AAA ACA GGA CCT GGG CAG AAA GCT ATA CTT TTT CTT CCA ATG TCT GCT
Lys Thr Gly Pro Gly Gln Lys Ala Ile Leu Phe Leu Pro Met Ser Ala
130                                          140

AAG AGC TGA TTT TAA
Lys Ser Ter     Ter
146
```

FIG. 4

```
     1                                            10
   phe asn leu pro leu gly asn tyr lys lys pro lys leu leu tyr cys ser    AMINO ACID SEQUENCE C            T       T  G       T       T    T
5' TTT AAT CTX CCX CTX GGX AAT TAT AAA AAA CCX AAA CTX CTX TAT TGT TCX    CODING SEQUENCE
                                                  TTA TTA        AGT
                                                          TTG 3' AAG TTG GAC GGG GAC CCG TTG ATG TTC TTC GGG TTC GAC GAC ATG ACG       PROBE 891

3' TTG ATG TTT TTT GGX TT 5'                      PROBES 853-856
   asn gly cys tyr phe leu arg ile leu pro asp gly thr val asp gly thr
                    20                                    30
                             C    T     T        T    T       T
5' AAT GGX TGT TAT TTT CTX CGX ATT CTX CCX GAT GGX ACX GTX GAT GGX ACX
                                 TTG AGA          C              TTG 3' TTA CCG ACG ATG AAG GAC GGA CTA CCG TGA CAC CTA CCG TGG               PROBES 889/890
```

FIG. 5